(12) United States Patent
Heintz

(10) Patent No.: US 6,605,594 B2
(45) Date of Patent: *Aug. 12, 2003

(54) AQUEOUS GLYCEROL FORMULATIONS OF SOMATOTROPIN

(75) Inventor: Daniel Nicholas Heintz, St. Louis, MO (US)

(73) Assignee: Monsanto Technology, LLC, St. Louis, MO (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/001,644

(22) Filed: Dec. 31, 1997

(65) Prior Publication Data

US 2003/0060404 A1 Mar. 27, 2003

Related U.S. Application Data

(60) Provisional application No. 60/033,971, filed on Dec. 31, 1996.

(51) Int. Cl.$^7$ .......................... A61K 38/00; A61K 38/27
(52) U.S. Cl. .................. 514/12; 514/2; 514/21; 530/399
(58) Field of Search ................. 514/2, 12, 21; 530/399

(56) References Cited

U.S. PATENT DOCUMENTS

| 4,855,141 A | | 8/1989 | Eckenhoff et al. | 424/423 |
|---|---|---|---|---|
| 4,857,506 A | * | 8/1989 | Tyle | 514/12 |
| 4,917,685 A | * | 4/1990 | Viswanathan et al. | 514/12 |
| 4,959,218 A | | 9/1990 | Eckenhoff et al. | 424/473 |
| 4,996,060 A | | 2/1991 | Eckenhoff et al. | 424/473 |
| 5,057,318 A | | 10/1991 | Magruder et al. | 424/473 |
| 5,079,230 A | * | 1/1992 | Randawa et al. | 514/12 |
| 5,567,677 A | * | 10/1996 | Castensson et al. | 514/12 |
| 5,597,797 A | * | 1/1997 | Clark | 514/12 |

FOREIGN PATENT DOCUMENTS

| EP | 0 213 851 | 3/1987 |
|---|---|---|
| EP | 303 746 | 2/1989 |
| EP | 373 867 | 6/1990 |
| EP | 0 374 120 | 6/1990 |
| EP | 374 120 | 6/1990 |
| EP | 586 085 | 3/1994 |
| WO | 92/17200 | * 10/1992 |
| WO | WO 9319776 | 10/1993 |
| WO | WO 93/19776 | 10/1993 |
| WO | WO 9512385 | 5/1995 |
| WO | WO 9514037 | 5/1995 |
| WO | WO 96/01123 | 1/1996 |

OTHER PUBLICATIONS

Abstract No. XP–002069690, "*Salt–Stabilized Protein Formulations*", Chemical Abstracts, vol. 122, No. 26, Columbus, Ohio (Jun. 26, 1995).

Abstract No. XP–002069691, Derwent Publications Ltd., London, GB, AN 89–192875 c25 (May 11, 1989).

Abstract No. 122:322396d, *Salt–stabilized protein formulation*, Anon. (UK), Res. Discl.. 1995, 370, 56–7 (Eng.).

* cited by examiner

Primary Examiner—Christopher S. F. Low
Assistant Examiner—Chih-Min Kam
(74) Attorney, Agent, or Firm—George R. Beck; Howrey Simon Arnold & White, LLP

(57) ABSTRACT

Aqueous somatotropin compositions are presented that contain less than about 10% of a biologically active somatotropin, water, and glycerol in an amount effective and at a pH effective to maintain the somatotropin substantially completely stable. The somatotropins in such compositions preferably retain their physical and chemical stability for at least 2 years. The somatotropin compositions also preferably have anti-microbial activity, such that, after they have been sterile-filtered, no additional anti-microbial agent is necessary to maintain the sterility of the composition.

16 Claims, No Drawings

AQUEOUS GLYCEROL FORMULATIONS OF SOMATOTROPIN

This application is related to U.S. Provisional Application Serial No. 60/033,971, filed Dec. 31, 1996.

BACKGROUND OF THE INVENTION

Somatotropins (growth hormones) were originally discovered in pituitary extracts of various animals, and may now be produced using recombinant DNA by conventional genetic engineering techniques. Somatotropins may be administered to animals using a variety of formulations and administration techniques. One major problem in the administration of somatotropins is the denaturation of their active globular structure, which may cause somatotropins to oligomerize (e.g., dimerize) and/or aggregate and precipitate, thereby decreasing the amount of available somatotropin in solution as well as the somatotropin bioactivity. Previously, formulations have been developed which incorporate a stabilizer in an attempt to decrease the formation of insolubles and maintain the bioactivity of the somatotropin.

For example, European Patent Application specification no. 374,120 (Monsanto Co.) refers to somatotropin compositions containing at least about 10% bioactive somatotropin, an effective amount of a stabilizing polyol, such as glycerol, and a buffer to achieve a pH in the range of 4.5 to either about 7 or the isoelectric point of the somatotropin, whichever is greater. This formulation is preferably administered to an animal from an implantable dispenser for controlled release over an extended period of time. The compositions of that specification preferably contain a bovine or porcine somatotropin.

There is a need in the art for novel somatotropin formulations that have good long term chemical and physical stability, preferably such that they qualify for FDA approval of labeling regarding long term shelf life. There is also a need for multi-dose somatotropin formulations that do not require additional anti-microbial agents to retain the stability and bioactivity of the formulation. Additionally, there is a need for somatotropin formulations that are especially suitable for parenteral administration to companion animals, such as dogs and cats.

SUMMARY OF THE INVENTION

This invention generally relates to aqueous glycerol formulations of a biologically active somatotropin. More particularly, this invention relates to aqueous somatotropin compositions comprising less than about 10% of a biologically active somatotropin, water, and glycerol in an amount effective and at a pH effective to maintain the somatotropin substantially completely stable. In a preferred embodiment, the somatotropins in such compositions retain their physical and chemical stability for at least 2 years. The somatotropin compositions according to the invention also have anti-microbial activity, such that, after they have been sterile-filtered, no additional anti-microbial agent is necessary to maintain the sterility of the composition.

In a preferred embodiment, the inventive somatotropin compositions are suitable for parenteral administration to companion animals, such as dogs and cats, and are preferably suitable for multiple dose packaging.

DESCRIPTION OF ILLUSTRATIVE EMBODIMENTS

For purposes of this invention, the term "somatotropin" includes mammalian somatotropins, such as human, ovine, porcine, bovine, equine, canine and feline somatotropins, particularly canine and feline somatotropins; and others such as avian somatotropin. The term "somatotropins" includes somatotropin proteins and salts thereof having naturally-occurring sequences as well as variants of the naturally-occurring proteins having somatotropin-like bioactivity. For example, "somatotropin" includes somatotropin proteins that have been modified at the N-terminus, e.g, by deleting an N-terminal methionine group or replacing it with another amino acid, or proteins that have other amino acid substitutions, additions or deletions but yet provide somatotropin-like activity, i.e., they bind to somatotropin receptors in the animal with sufficient affinity to result in improvement of growth, lactation, feed efficiency and/or health of the animal.

The somatotropins for use in the present invention can be derived by extraction and subsequent concentration techniques from the pituitary glands of various animals. More preferably, somatotropins produced by recombinant DNA methods are used in the inventive compositions. The somatotropin to be formulated can be a heavy metal (e.g., zinc) derivative of the somatotropin, or it can be free from association with such a metal. The somatotropin to be formulated can also be a powder (e.g., lypholized) or in aqueous solution.

The proportion of somatotropin in the inventive compositions may vary, for example, depending upon the size and type of animal being treated as well as the desired dosage and treatment strategy. The somatotropin content of the inventive composition is less than about 10% by weight of the composition. The composition preferably has a somatotropin content of less than about 8% by weight of the composition, more preferably less than about 6%. In further preferred embodiments, the composition has a somatotropin content of at least about 0.01%, preferably at least about 0.3% by weight; up to about 5% and commonly up to about 3% by weight.

The inventive compositions further contain water and glycerol, preferably in an amount such that the glycerol:water volume ratio is not less than about 1:1 to ensure anti-microbial activity, and not greater than about 4:1, to facilitate an efficient sterile filtration rate.

Generally, the pH of the inventive aqueous glycerol somatotropin composition is between about 4.5 and the greater of about 7 and about the isoelectric point of the somatotropin. More preferably, the pH of the composition is in the range of about 6 to about 7.

In a preferred embodiment, the inventive formulation further contains one or more additives such as a surfactant, a wetting agent and/or an anti-foaming agent. For example, a non-ionic surfactant may be added in an amount sufficient to lower the surface tension and yet minimize adverse site reactions. For example, the surfactant additive may be a polyethoxylated sorbitan ester, such as a tri(polyoxyethylene) ester of sorbitan mono-oleate (available as Tween 80 from ICI Americas Inc.), which may also act as a wetting agent to promote the wetting of the somatotropin by a buffer and glycerol excipient during preparation and may further prevent foaming. The surfactant can be present in a concentration ranging from about 0.005% to about 2.5%, and more preferably from about 0.05% to about 1.0% of the composition.

The inventive aqueous glycerol formulations of somatotropin are chemically and physically stable and substantially completely retain the bioactivity of the somatotropin. The inventive formulations preferably remain stable for at least 2 years, more preferably at least 3 years and most preferably for at least 4 years. This stability characteristic is determined by observing the formulations for dimer and aggregate formation, as well as for turbidity, at various temperatures over a period of time, which simulates the long term performance of the formulation stability. A formulation is considered substantially completely stable if less than 10% of the somatotropin is found in the form of dimer and aggregates after storage of the formulation at 4° C. for 2 years, and visibly remains clear and does not settle out during such storage.

The inventive aqueous glycerol formulations have anti-microbial activity, and accordingly, no further anti-microbial agent or preservative need be added to the composition. The anti-microbial activity of the inventive formulations is largely due to the high glycerol content. The inventive aqueous glycerol formulations are also usually subjected to sterile filtration.

In a preferred embodiment, the aqueous glycerol formulations of somatotropin according to the invention are suitable for parenteral administration to companion animals, particularly to dogs and cats. For example, the inventive somatotropin composition may contain canine somatotropin and be administered to dogs for the treatment of alopecia, bone fractures and other injuries and diseases suitably treated using the cell proliferation and other biological activities of a somatotropin. In a further preferred embodiment, the aqueous glycerol formulations are adequate compositions for a commercial multi-dose product. These formulations can be administered in a variety of ways, including parenteral administration, such as subcutaneous, intramuscular or intraperitoneal techniques or via an implanted delivery device. For companion animals, the preferred method of administration is parenteral administration via subcutaneous injection.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Example 1

Preparation of Aqueous Glycerol Formulation of Porcine Somatotropin 10.5 g of pST powder was added to 1 L of an excipient (65:35, glycerol: water by volume, 0.15% Tween 80 surfactant by volume, pH 6.3 phosphate buffer and 3% potassium chloride by weight) and the mixture was stirred for ½ hour at ambient temperature. This formulation was then sterile filtered through a 0.22 $\mu$m filter.

Example 2

Preparation of Excipient 3.747 kg of WFI (water for injection) was added to a vessel and agitated at moderate r.p.m. The vessel was then charged with sodium phosphate monobasic (0.143 kg), sodium phosphate dibasic (0.175 kg) and potassium chloride (0.252 kg). The resulting mixture was stirred until all solids dissolved. This dissolution was endothermic and the mixture cooled to 15–20° C. The vessel was then further charged with 7.665 kg of glycerol and 0.0182 kg of Tween 80. The mixture warmed up to about 30° C. The mixture was then cooled to a temperature of 20–25° C. by cooling coils/jacket and agitation.

A 50–55 g sample was then removed and analyzed. The sample was a clear, colorless liquid having a pH at 20–25° C. of 6.1–6.6 and a density at 22° C. of 1.20±0.02 g/cc.

Example 3

Preparation of Bovine Somatotropin Formulation

The excipient prepared in Example 2 was stirred at a temperature of 20–25° C. ZnbST in the form of bulk powder (0.0521 kg) was then added over a period of 20–30 minutes. After all of the ZnbST powder was added, the mixture was stirred for an additional 50–60 minutes at 20–25° C. During this period, the excipient turned turbid due to the formation of zinc phosphate salts. The mixture was then heated to 36–40° C. for 80–100 min. Subsequently, the mixture was cooled to 20–25° C. and stirred for at least 30 minutes.

The bST/excipient formulation was then filtered by connecting a Millipore Millipak-200, 0.22 $\mu$m disposable filter unit to the discharge port of the formulation vessel. The formulation vessel was placed under a regulated air pressure of 15 psig and the discharge port was opened. The filtration was complete in less than 15 minutes with a small decrease in the filtration rate over the cycle time.

Example 4

Stability Testing of Aqueous Glycerol Formulation of bST

Samples of aqueous glycerol formulations of bovine somatotropin were stored for periods of time up to 120 days at temperatures of 4° C., 22° C. and 39° C.

Chemical stability was evaluated based on dimer/aggregate formation. The formulation according to the invention had no detectable dimer or aggregate formation at 4° C. or 22° C. for up to 75 days, which is very atypical and unusually stable for storage of such formulations, particularly at 22° C. About 2% dimer/aggregate formation occurred at 39° C. at the 75th day, which is a surprisingly good result at such a high temperature in having a low dimer/aggregate formation.

Physical stability was evaluated based on the turbidity of the samples. The formulation according to the invention had no visually observable turbidity change at 4° C. or 22° C. for up to 120 days, which is very atypical and unusually stable, particularly at 22° C. Signs of very slight turbidity were observed after 20–22 days at 39° C. This stability is still considered extremely good.

While the compositions and methods of this invention have been described in terms of preferred embodiments, it will be apparent to those of skill in the art that variations may be applied to the process described herein without departing from the concept, spirit and scope of the invention. All such similar substitutes and modifications apparent to those skilled in the art are deemed to be within the spirit, scope and concept of the invention.

What is claimed is:

1. An injectable aqueous glycerol somatotropin composition comprising:

a biologically active somatotropin in a concentration less than 6% by weight of the composition, a surfactant, water and glycerol in an amount effective and at a pH effective to maintain the somatotropin substantially completely stable;

wherein the ratio of glycerol to water, by volume, is about 1:1 to 4:1.

2. The composition of claim 1, wherein the somatotropin is bovine somatotropin, porcine somatotropin, ovine somatotropin, equine somatotropin, canine somatotropin or feline somatotropin.

3. The composition of claim 2, wherein the somatotropin is canine somatotropin or feline somatotropin.

4. The composition of claim 1, wherein the composition has a pH of about 4.5 to either about 7 or about the isoelectric point of the somatotropin, whichever is greater.

5. The composition of claim 4, wherein the composition has a pH of about 6 to about 7.

6. The composition of claim 1, wherein the surfactant is a non-ionic surfactant.

7. The composition of claim 6, wherein the non-ionic surfactant is present in a concentration of about 0.05% to about 1.0% by weight of the composition.

8. The composition of claim 6, wherein the non-ionic surfactant comprises a polyethoxylated sorbitan ester.

9. The composition of claim 8, wherein the non-ionic surfactant is a tri(polyoxyethylene)ester of sorbitan mono-oleate.

10. The composition of claim 1, wherein the composition is substantially completely stable for at least 2 years.

11. The composition of claim 1, wherein the composition is sterile.

12. The composition of claim 1, wherein the composition contains no additional anti-microbial agent.

13. The composition of claim 1, wherein the somatotropin is present in a concentration of about 0.01% to about 5% by weight of the composition.

14. The composition of claim 1, wherein the somatotropin is present in a concentration of about 0.3% to about 3% by weight of the composition.

15. The composition of claim 1, wherein:

the somatotropin is canine somatotropin or feline somatotropin;

the somatotropin is present in a concentration of about 0.3% to about 3% by weight of the composition; and the pH is about 4.5 to either about 7 or about the isoelectric point of the somatotropin, whichever is greater.

16. An injectable aqueous glycerol somatotropin composition suitable for parenteral administration comprising:

a biologically active somatotropin in a concentration of about 0.01% to about 3.0% by weight of the composition, a surfactant, water and glycerol in an amount effective and at a pH effective to maintain the somatotropin substantially completely stable;

wherein the ratio of glycerol to water, by volume, is about 1:1 to 4:1.

* * * * *